United States Patent [19]

Shiber

[11] Patent Number: 4,894,051
[45] Date of Patent: Jan. 16, 1990

[54] ATHERECTOMY SYSTEM WITH A BIASING SLEEVE AND METHOD OF USING THE SAME

[75] Inventor: Samuel Shiber, Mundelein, Ill.

[73] Assignee: Surgical Systems & Instruments, Inc., Mundelein, Ill.

[21] Appl. No.: 286,509

[22] Filed: Dec. 19, 1988

Related U.S. Application Data

[63] Continuation-in-part of Ser. No. 243,900, Sep. 13, 1988, which is a continuation-in-part of Ser. No. 78,042, Jul. 27, 1987, Pat. No. 4,818,634, and a continuation-in-part of Ser. No. 205,479, Jun. 13, 1988, and a continuation-in-part of Ser. No. 225,880, Jul. 29, 1988, Pat. No. 4,842,579, which is a continuation-in-part of Ser. No. 18,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.[4] .............................................. A61B 17/32
[52] U.S. Cl. ....................................... 604/22; 606/159
[58] Field of Search ................ 128/305, 304, 753, 754; 604/22

[56] References Cited

U.S. PATENT DOCUMENTS

| | | | |
|---|---|---|---|
| 4,627,436 | 12/1986 | Leckrone | 128/303.1 |
| 4,669,469 | 6/1987 | Gifford et al. | 128/305 |
| 4,772,258 | 9/1988 | Marangoni et al. | 604/22 |
| 4,781,186 | 11/1988 | Simpson et al. | 128/305 |
| 4,794,931 | 1/1989 | Yock | 128/305 |

*Primary Examiner*—Michael H. Thaler
*Attorney, Agent, or Firm*—Samuel Shiber

[57] ABSTRACT

An atherectomy system for removing an obstruction from within a patient's vessel, comprising a flexible guide-wire insertable into the vessel, a flexible catheter for coring and ingesting obstruction material, insertable into the vessel over the flexible guide-wire, the flexible catheter having a coring device at its distal end and coupling device for connecting it to a power source, at its proximal end, a sleeve in which the flexible catheter is slidably disposed, the sleeve having an elongated tongue extending from its distal end, the tongue defining inside the vessel an eccentrically biased trajectory for the coring device to move along.

24 Claims, 3 Drawing Sheets

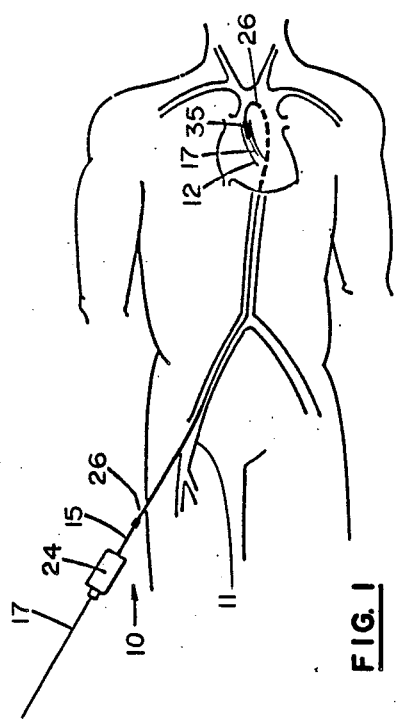
FIG. 1
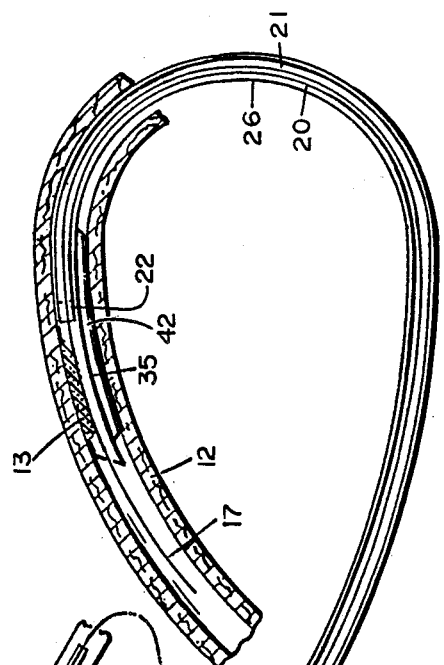
FIG. 2
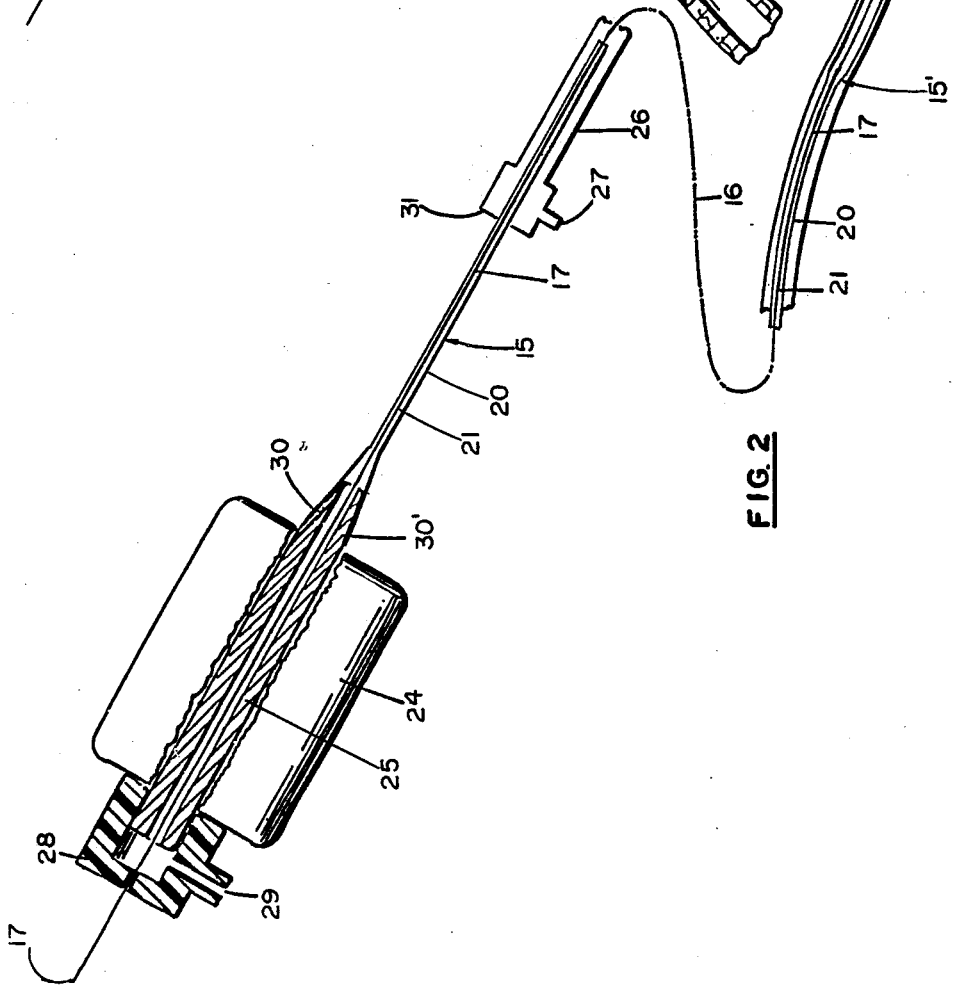

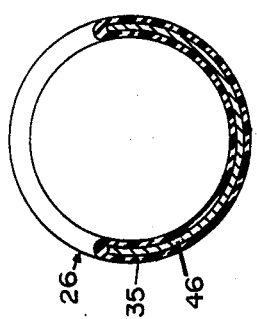
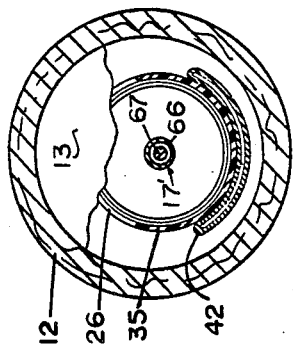
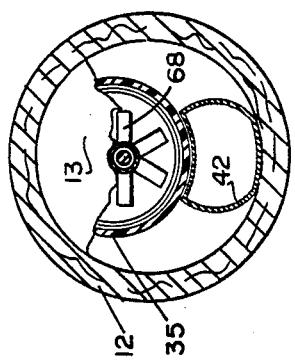
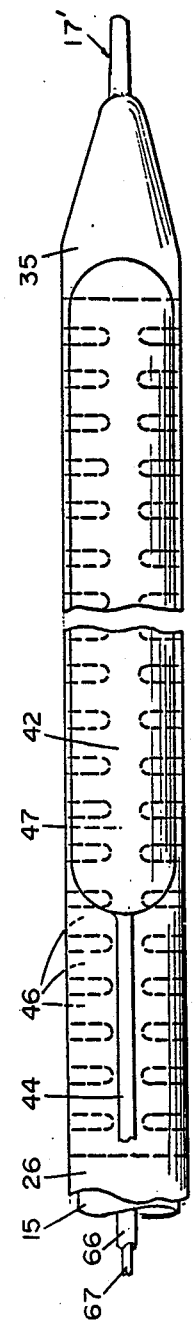
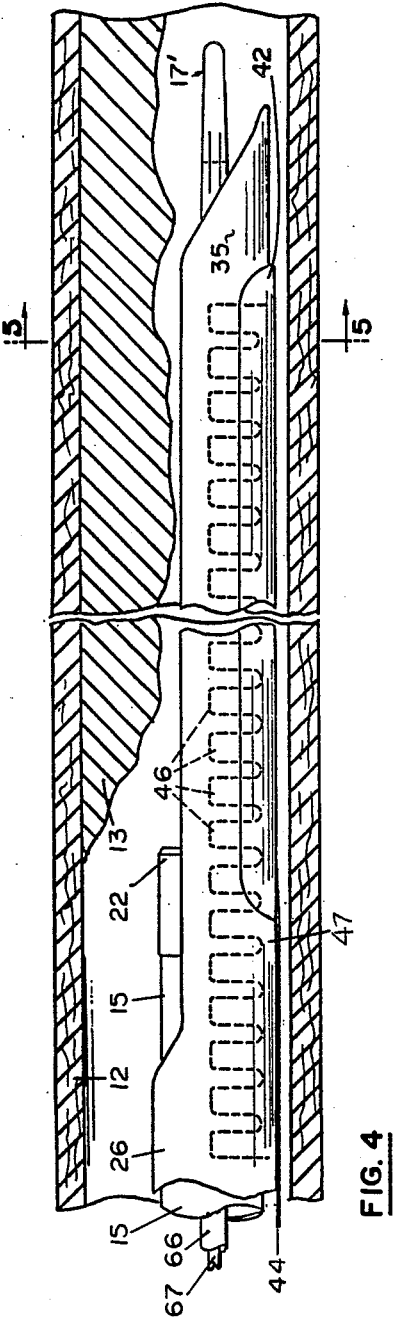
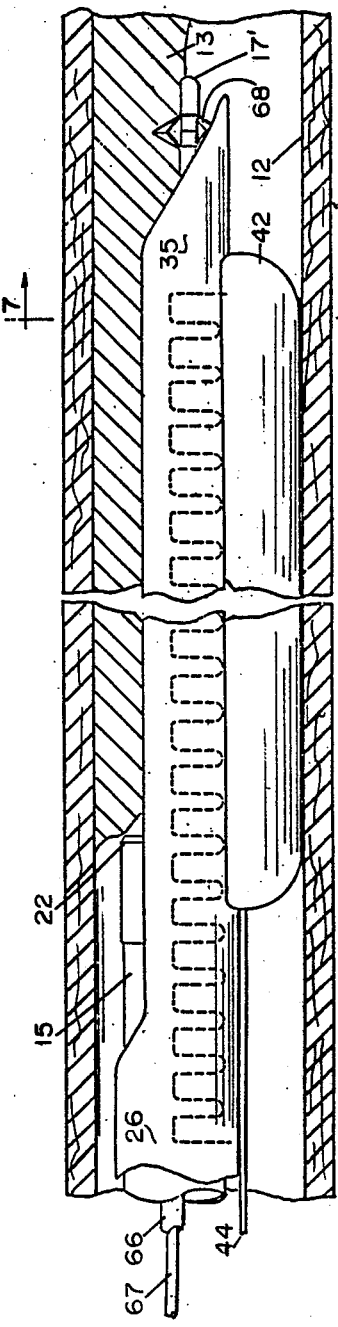

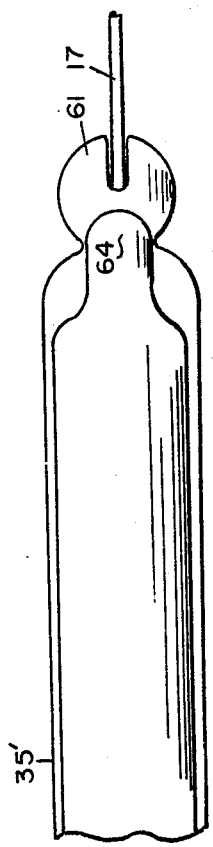
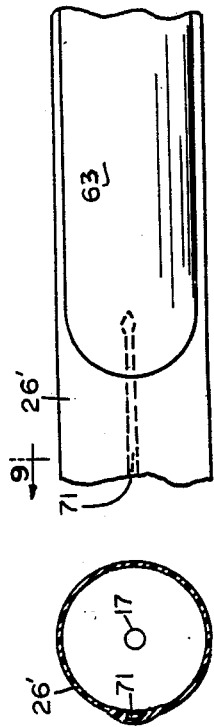
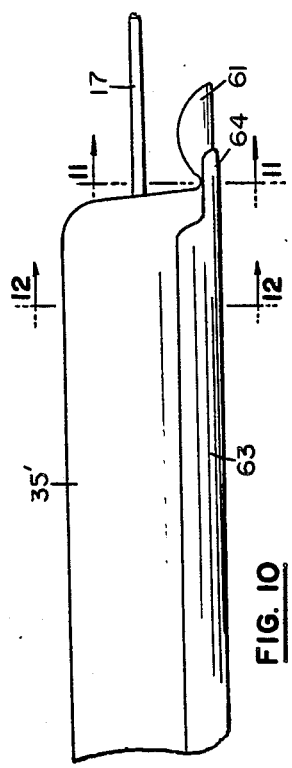
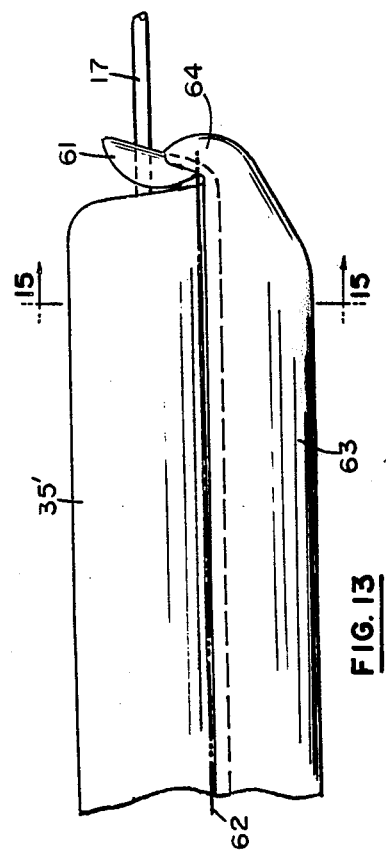
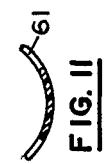
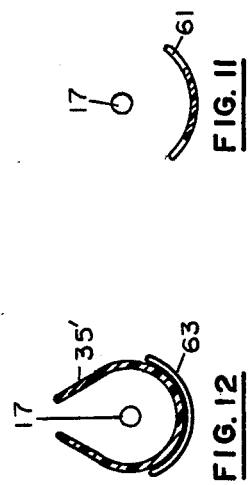
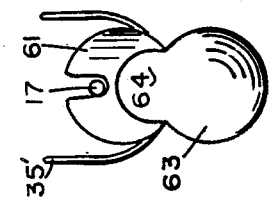
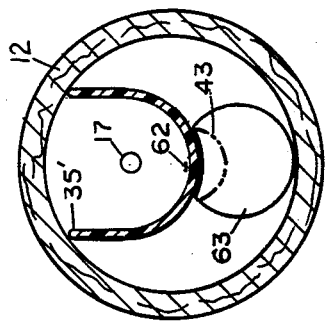

ATHERECTOMY SYSTEM WITH A BIASING SLEEVE AND METHOD OF USING THE SAME

CROSS REFERENCE TO OTHER APPLICATIONS

This application is a continuation-in-part (CIP) of application Ser. No. 243,900 filed 9/13/88 which is a continuation-in-part of three applications, application Ser. No. 078,042 filed 7/27/87 (now patent No. 4,819,634), application Ser. No. 205,479 filed 6/13/1988 and application 225,880 filed 7/29/88 (now patent No. 4,842,257). These three applications are continuation-in-parts of application Ser. No. 018,083 filed 2/24/1987, which is a continuation-in-part of application Ser. No. 874,546 filed 6/16/1986 (now patent 4,732,154) which is a continuation-in-part of application Ser. No. 609,846 filed 5/14/1984 (abandoned).

BACKGROUND OF THE INVENTION

With age a large percentage of the population develops atherosclerotic arterial obstructions resulting in a diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (angioplasty). Some of the problems with angioplasty are that it injures the arterial wall, it creates a rough lumen and in substantial number of the cases it is ineffective. Further, angioplasty does not remove the obstruction material out of the arterial system, therefor in a case of a heart attack, immediate angioplasty carries the risk of dislodging the blood clot and allowing it to move down stream creating additional blockages.

An objective of the present invention is to provide an atherectomy catheter which is insertable and advancable in an artery over a flexible guide-wire. The flexible catheter is equipped with a coring means at its distal end to core and extract obstruction material and create a smooth lumen without cracking the arterial wall. The catheter is slidable in an eccentrically biasing sleeve that defines the catheter's trajectory in the vessel in order to selectively aim the coring means into the obstruction. This allows the treatment of eccentric lesions and the utilizing of the system in larger arteries without increasing the flexible catheter's diameter and the associated puncture wound at the point of insertion of the system into the vessel.

These and other objectives of the invention will become apparent from the following discussion and the accompanying drawings.

BRIEF DESCRIPTION OF THE FIGURES

FIG. 1 schematically shows a general view of an atherectomy system inserted at the groin area, through a patient's arterial system, into his coronary artery.

FIG. 2 shows a cross sectioned view of the atherectomy system. The middle portion of the system is represented with a phantom line, due to space limitations on the drawing sheet.

FIG. 3 shows a bottom view of a distal portion of a first embodiment of the system.

FIG. 4 shows a side view of a distal portion of the first embodiment, in an artery, prior to pressurizing an inflatable chamber through an inflatable tube and prior to expanding a barrier means at the distal end of the flexible guide-wire.

FIG. 5 shows a cross sectional view along line 5—5 marked on FIG. 4 of the first embodiment, in an artery, prior to pressurizing an inflatable chamber.

FIG. 5' shows a cross sectional view along line 5—5 marked on FIG. 4 of the tongue of the first embodiment, on an enlarged scale, showing the reinforcing rib.

FIG. 6 shows a side view of a distal portion of the first embodiment, in an artery, with the inflatable chamber and the inflatable tube pressurized and with the distal barrier means expanded.

FIG. 7 shows a cross sectional view along line 7—7 marked on FIG. 6 of the first embodiment, in an artery, with the inflatable chamber pressurized and with the distal barrier means expanded.

FIG. 8 shows a bottom view of a distal portion of a biasing sleeve of a second embodiment of the system.

FIG. 9 shows a cross sectional view along line 9—9 marked on FIG. 8, of the biasing sleeve with an inflation passage formed in its wall.

FIG. 10 shows a side view of a distal portion of a biasing sleeve of the second embodiment of the system.

FIG. 11 shows a cross sectional view along line 11—11 marked on FIG. 10, of the gate.

FIG. 12 shows a cross sectional view along line 12—12 marked on FIG. 10, of the tongue.

FIG. 13 shows a side view of a distal portion of the tongue of the second embodiment of the system with a pressurized inflatable chamber and a closed gate.

FIG. 14 shows a front view of a distal end of the tongue with a pressurized inflatable chamber and a closed gate.

FIG. 15 shows a cross sectional view along line 15—15 marked on FIG. 13, of the tongue of the second embodiment of the system with a pressurized inflatable chamber biasing the tongue, in an artery.

DETAILED DESCRIPTION OF THE DRAWINGS

FIG. 1 schematically shows a general view of an atherectomy system with a biasing sleeve, 10, introduced percutaneously (through the skin) into a patient's femoral artery 11 at the groin area. The system's distal end is inserted through the arterial system to reach a work site in a coronary artery 12 and its proximal end remains outside the patient's body.

As shown in FIG. 2 the atherectomy system comprises several elongated parts in a nested relationship, and their ends shall be referred to as "distal" meaning the end which goes into the vessel and "proximal" meaning the other end. In view of the above, "distal direction" or "distally" shall indicate a general direction from the proximal end to the distal end, and "proximal direction" or "proximity" shall refer to an opposite direction.

As further shown in FIG. 2, the distal portion of the system 10 is placed in the diseased coronary artery 12 (same numbers are used to indicate similar items through the FIGURES) containing an eccentric atherosclerotic obstruction 13. The system's mid portion is represented by a phantom line 16 because of space limitation of the drawing sheet.

The system comprises:

A flexible guide-wire 17 insertable through the human vascular system.

A flexible rotary-catheter 15, rotatable and slidable over the guide-wire, having a wall 20 defining a longitudinal channel 21. Coring means is the form of a tubular blade 22 is mounted at the distal end of the flexible rotary-catheter. The tubular-blade defines a through-hole forming with the channel 21 a continuous passage for accepting the obstruction material ingested into the through-hole. Alternate suitable coring means which utilize radiation, heat or teeth are discussed in my copending patent applications incorporated above.

Frictional losses which develop between the flexible rotary-catheter and a biasing sleeve 26 strain the flexible rotary-catheter and the motor. These frictional loses are more pronounced with an obese patient where the system is introduced into the femoral artery at the groin and has to assume a sharp bend at the point of entry due to patient's protruding absomen. To reduce these frictional losses the diameter of the proximal portion of the flexible rotary-catheter is decreased at a point marked 15' on FIG. 2. Such a diametrical decrease does not interfere with the ingestion of obstruction material as long as a sufficient distal portion of a full diameter flexible rotary-catheter is left to accept the material. For example, a flexible rotary-catheter for removing an obstruction from peripheral arteries having a total length of 50 centimeters (cm) can be manufactured with a 35 cm proximal portion of 2 millimeters (mm) diameter and a 15 cm distal portion of 3 mm diameter. However, if the obstruction is long the location of the diametrical transition point 15' can be moved proximally to increase the catheter's material ingestion capacity.

A motor 24 has a hollow shaft 25 with a tapered distal end 30' which engages a coupling means in the form of a matching tapered seat 30 formed at the proximal end of the flexible rotary-catheter.

The biasing sleeve 26 has a tongue with biasing means, which defines inside the vessel an eccentric trajectory for the coring means to move along. The sleeve can also serve as an introducer of the system into the artery, or it can be introduced through a separate introducer sheath. Further, the sleeve can be formed to a desired shape to serve as a guiding-catheter to assist in delivering the flexible rotary-catheter to the work site. Additionally, the biasing sleeve has a port 27 through which it accepts contrast or irrigating/lubricating fluids and delivers them through its distal end to the work site. A seal 31 prevents the fluid from escaping out through the sleeve's proximal end.

A rotary joint 28 has a port 29 which is connected through the hollow shaft 25 to the continuous passage and can be used for introducing a negative pressure in the continuous passage to assist in sucking and drawing the cored obstruction material into it. The suction and a mechanical action resulting from the relative motion between the rotating inner wall of the continuous passage and the stationary flexible guide-wire effectively ingests the cored material into the continuous passage for subsequent removal out of the patient's body. In an early stage of the procedure, prior to ingesting obstruction material, the fluid rate connecting the port 29 and the distal end of the flexible rotary-catheter can be used as an alternative route for delivering fluids to the work site.

The flexible guide-wire slidabley passes through a close fitting hole formed at the end of the rotary joint.

FIGS. 3 to 7 show the distal end of an atherectomy system with a first embodiment of a biasing sleeve for removing an obstruction from within the patient's vessel, artery 12, comprising:

the flexible guide-wire 17', the flexible rotary-catheter 15 with coring means in the form of the tubular-blade 22 at its distal end, for coring and ingesting obstruction material, insertable into the vessel over the flexible guide-wire.

A biasing sleeve 26 in which the flexible rotary-catheter is rotatably and slidably disposed and an elongated tongue 35 which extends from the distal end of the biasing sleeve and defines, inside the vessel, an eccentric trajectory for the flexible rotary-catheter and the coring means to move and core along.

In the first embodiment the tongue has cross section in the shape of an incomplete circle, shown in FIGS. 5, 5' and 7, which positively contains the flexible rotary-catheter by surrounding slightly more than half of its periphery. The tongue's cross section is stabilized by reinforcing means in the form of semicircular ribs like elements 46 (note FIG. 5'). The elements 46 are tied together by a spine like element 47 which contributes substantially to the strength and the stiffness of the tongue in resisting twisting under torque, while allowing it to bend. Therefore, elements 46 and 47, which can be made from flat stainless steel sheet material, stabilize the cross section of the tongue to maintain the proper relationship between the tongue cross section and the tubular-blade but allow the tongue to bend and conform to the arterial curvature. They also enable the user to rotate the tongue in the artery to position and reposition its top, open side toward the obstruction which is to be removed.

The tongue has a selectively actuable biasing means in the form of an inflatable chamber 42 for eccentrically biasing it in the vessel in order to define, inside the vessel, the eccentrically biased trajectory for the coring means and the flexible rotary-catheter to move and core along. The tongue enables the user to direct the coring means along eccentric lesions and to utilize the system for re-canalizing larger arteries. Re-canalizing larger arteries is done by curing while biasing the coring means with the tongue towards one side of the artery, then backing the coring means, rotating the sleeve and the tongue a part of a turn in the artery, rebiasing the tongue by inflating the chamber 42 and making another pass, repeating the procedure and making additional passes as needed. Thus, a large diameter artery can be debulked and re-canalizing through a smaller puncture wound in the vessel's wall.

An inflatable tube 44, for inflating the chamber 42, is formed integral with the chamber. When the chamber is inflated the tube is also slightly inflated, as shown in FIG. 6, however, prior to inflation the tube remains flat (negative pressure can be applied to the tube to further reducing its dimensions) as shown in FIG. 4, minimizing its contribution to the overall thickness of the biasing sleeve structure and to the size of puncture wound that will be needed to introduce the structure into the patient's body.

The flexible guide-wire 17' has a distal barrier means in the form of thin jacket over a core wire 67. The jacket and core wore are bonded at their distal tip, and by pulling the core wire relative to the jacket at the proximal tip, arms 68 which are formed by multiple slits in the sleeve, are extended radially. Barrier means as well as additional suitable flexible guide-wire designs are discussed in my copending patent applications incorporated above.

In the second embodiment of the biasing sleeve 26', shown in FIGS. 8 to 15, the tongue 35' has a "U" shaped cross section which acts to define inside the vessel an eccentrically biased trajectory for the coring means to move along which positively holding the arterial wall out of this trajectory, thereby minimizing the probability of cutting into the arterial wall (note FIG. 15).

The tongue of the second embodiment 35' has a selectively variable cross section to facilitate its insertion in a folded position as shown in FIG. 12 to minimize the size of the puncture wound that is required to introduce the system into the vessel. At the obstruction site the tongue unfolds in response to inflation of a inflatable chamber 63 which is externally attached to a bottom side of the tongue 35', as shown in FIG. 15. The inflatable chamber 63 also serve to bias the U-shaped tongue towards the arterial wall, however, if the tongue is biased and contacts the wall before being unfolded, the contact with the wall may interfere with the unfolding process. Optionally, a smaller inflatable chamber 43 can be nested, as shown in FIG. 15 in a phantom line, in the inflatable chamber 63, to unfold the tongue when it is inflated. Due to its smaller size chamber 43 is less likely to energize the tongue against the wall. When the unfolding process is completed the inflatable chamber 63 can be inflated to accomplish the biasing of the tongue. A passage 71 which is formed in a wall of the sleeve 26', as shown in FIGS. 8 and 9, has a distal end communicating with the chamber 63 for delivering inflating fluid thereto.

The tongue 35' has a gate 61 at its distal end, to minimize escapement of obstruction material distally. The gate is selectively acutable by a distal narrowed end 64 of the inflatable chamber 63 which acts as an actuator closing the gate to the position shown in FIG. 13, when inflated. Alternatively, a mechanical means in the form of a strip 62 made, preferably from a stainless steel, shown in a phantom line on FIG. 13, can be used to close the gate 61.

OPERATION

A process for removing an obstruction from a vessel with an atherectomy system, comprises the following steps:

Inserting into an obstruction in a vessel a flexible guide-wire (the technique for inserting guide wires through the vascular system is well established).

Advancing over the flexible guide-wire a flexible catheter having a coring means at its distal end, to the vicinity of the obstruction.

Coring an initial lumen in the obstruction and ingesting the cored material in the catheter. Retracting the coring means from the initial lumen and inserting a biasing tongue into it.

Advancing the flexible catheter and coring the obstruction along an eccentrically biased trajectory defined by the tongue. The amount of biasing can be regulated by the inflation pressure of a chamber attached to the bottom of the tongue.

In a case where the diseased lumen is large enough to accept the tongue the step of coring an initial lumen can be skipped.

Negative pressure can be used to assist the mechanical action in enabling the cored obstruction material into the continuous passage.

It should be noted that the atherectomy system can be manufactured in different diameters and lengths depending on the size and site of artery that it is intended for and on whether the system is to be used percutaneously (that is through the skin) or intra-operatively (that is when the vessel is surgically exposed for inserting the system into the vessel).

It can also be noted from the present application and the incorporated applications that components of the atherectomy system can be made in several ways: The flexible catheter can be made from plastic or metal and either version can be equipped with an interal helical step. The coring means can be a tubular-blade, a heated tubular blade or a radition emitting means such as an optical fiber located at a wall of the flexible catheter carrying laser energy, or other means which core and ingest an obstruction placed in front of it. By combining a biasing sleeve with certain features, a flexible catheter with certain features and a flexible guide-wire with certain features a variety of species can be made to match the system's characteristics with the specific disease characteristics oof the individual patient, which is helpful, since the clinical characteristics of arterial atherosclerotic obstructions vary in geometry, hardness, and accessibility from one patient to another. Therefore, it should be understood that various modifications and substitutions may be made without deparing from the spirit of the invention or the scope of the claims.

I claim:

1. An atherectomy system for coring, ingesting and removing an obstruction from within a patient's vessel, comprising in combination:
   a flexible guide-wire insertable into the vessel,
   a flexible rotary catheter, rotably disposed and insertable into the vessel over said flexible guide-wire, having at its distal end a rotary coring means for making a circular cut in an obstruction located in front of it, and coupling means at its proximal end,
   a continuous passage, for ingesting the cored obstruction material, defined between said flexible rotary catheter and said flexible guide-wire, where the relative motion between said flexible rotary catheter and said flexible guide-wire assists in moving said ingested obstruction material proximally in said continuous passage, and,
   a sleeve in which said flexible catheter is slidably disposed, said sleeve having an elongated tongue extending from its distal end, said tongue defining inside said vessel an eccentrically biased trajectory for said coring means to move along.

2. An atherectomy system as in claim 1, said tongue has a circular cross section which positively contains said flexible catheter.

3. An atherectomy system as in claim 1, said tongue has a U shaped cross section.

4. An atherectomy system as in claim 1, said tongue having a selectively variable cross section to facilitate insertion thereof into the vessel.

5. An atherectomy system as in claim 1, said tongue's cross section being selectively variable and adapted to unfold in response to inflation of a chamber means which is attached externally to a bottom side of said tongue.

6. An atherectomy system as in claim 1, said tongue's cross section is stabilized by reinforcing means.

7. An atherectomy system as in claim 1, said tongue having a selectively actuable biasing means for eccentrically biasing said tongue in the vessel.

8. An atherectomy system as in claim 7, said biasing means comprise an inflatable chamber attached in bottom side of said tongue.

9. An atherectomy system as in claim 1, said tongue has a gate at its distal end.

10. An atherectomy system as in claim 9, said gate is selectively acutable by mechanical means.

11. An atherectomy system as in claim 9, said gate is selectively acutable by inflatable chamber means.

12. An atherectomy system as in claim 1, wherein suction is applied at said proximal end of said continuous passage to pull the cored obstruction material proximally in said continuous passage.

13. An atherectomy system as in claim 1, said coring means being a rotating tubular-blade.

14. An atherectomy system as in claim 1, said flexible catheter being a flexible rotary-catheter.

15. An atherectomy system as in claim 14, said flexible rotary-catheter having a decreased diameter at its proximal section to reduce frictional losses between said flexible rotary-catheter and said sleeve at the area of entering the patient's body.

16. An atherectomy system as in claim 1, said coring means being a radiation emitting device.

17. An atherectomy system as in claim 1, said flexible guide-wire having radially extending distal barrier means to counter distal movement of obstruction material.

18. An atherectomy system as in claim 17, wherein said distal barrier means can elastically contract to pass through a narrowed lumen.

19. An atherectomy system as in claim 41, wherein said distal barrier means are selectively expandable.

20. An atherectomy system as in claim 1, wherein means for introducing fluids into the vessel are connected to said sleeve.

21. A proces for removing an obstruction from a vessel with an atherectomy system, comprising the following steps:
  inserting into a vessel, into an obstruction, a flexible guide-wire,
  advancing over the flexible guide-wire a flexible chamber equipped with coring means at its distal end and a sleeve having a tongue extending from its distal end,
  placing said tongue along the obstruction,
  advancing the coring means to the obstruction,
  advancing the flexible catheter and coring along an eccentrically biased trajectory defined by the tongue while coring and ingesting into the flexible catheter the obstruction material,
  removing the flexible catheter and ingested obstruction material out of the vessel.

22. A process as in claim 21, wherein suction is used to enable the cored obstruction material into the continuous passage.

23. A process for removing an obstruction from a vessel with an atherectomy system, comprising the following steps:
  inserting into a vessel, into an obstruction, a flexible guide-wire,
  advancing over the flexible guide-wire a coring means and coring an initial lumen in the obstruction,
  retracting the coring means from said initial lumen,
  inserting a tongue into said initial lumen,
  advancing the flexible catheter and coring along an eccentrically biased trajectory defined by the tongue while coring and ingesting into the flexible catheter the obstruction material, to enlarge the initial lumen.

24. A process as in claim 23, wherein suction is used to enable the cored obstruction material into the continuous passage.

* * * * *